United States Patent [19]

Kimata et al.

[11] Patent Number: 5,155,124
[45] Date of Patent: Oct. 13, 1992

[54] TRIAZOLE COMPOUND AND INSECTICIDE COMPOSITION CONTAINING THE SAME

[75] Inventors: Toshiya Kimata; Tetsuo Tsuruya; Shunji Hayashi; Kazuhiro Kojima; Satoshi Yamanaka, all of Tokyo; Kiyoshi Sakuma, Honjo, all of Japan

[73] Assignee: S.D.S. Biotech K.K., Tokyo, Japan

[21] Appl. No.: 528,384

[22] Filed: May 25, 1990

[30] Foreign Application Priority Data

May 26, 1989 [JP] Japan .................. 1-131281
Dec. 19, 1989 [JP] Japan .................. 1-327165

[51] Int. Cl.$^5$ .................. A01N 43/653; C07D 249/12
[52] U.S. Cl. .................. 514/384; 514/212; 514/326; 540/603; 546/210; 548/264.4
[58] Field of Search .................. 514/384, 212, 326; 548/264.2, 264.4; 546/210; 540/603

[56] References Cited

U.S. PATENT DOCUMENTS 3,794,661  2/1974  Boehner et al. .................. 548/264.4
4,265,897  5/1981  Gsell et al. .................. 548/264.4

Primary Examiner—Patricia L. Morris
Attorney, Agent, or Firm—Sughrue, Mion, Zinn, Macpeak & Seas

[57] ABSTRACT

A triazole compound having the formula (I):

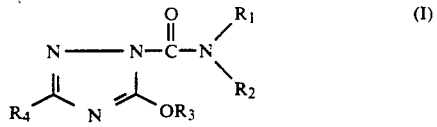

wherein $R_1$ and $R_2$ represent a hydrogen atom, a lower alkyl group or a dialkylcarbamoyl group, or $R_1$ and $R_2$ may be bonded to form an alkylene group, an oxyalkylene group or a thioalkylene group which may be substituted with a lower alkyl group, $R_3$ represents a hydrogen atom or CONRR' where R and R' represent an alkyl group, an alkenyl group, an alkynyl group, a cyanoalkyl group or a phenyl group or benzyl group which may be substituted, or R and R' may be bonded to form an alkylene group, an oxyalkylene group or a thioalkylene group which may be substituted with a lower alkyl group; $R_4$ represents

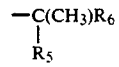

where $R_5$ represents a hydrogen atom, a lower alkyl group or a phenyl group, $R_6$ represents a lower alkyl group, or $R_5$ and $R_6$ may be bonded to form an alkylene group, with a proviso that $R_1$ and $R_2$ cannot be dialkylcarbamoyl groups at the same time, and an insecticide containing the triazole compound as an active component.

10 Claims, No Drawings

TRIAZOLE COMPOUND AND INSECTICIDE COMPOSITION CONTAINING THE SAME

BACKGROUND OF THE INVENTION

1. Field of the Invention

The present invention relates to a triazole compound having the formula (I), and an insecticide composition containing this compound as the active ingredient.

In the formula (I), $R_1$ and $R_2$ represent a hydrogen atom, a lower alkyl group having 1 to 6 carbon atoms or a dialkylcarbamoyl group having $C_1$–$C_6$ alkyl group, or $R_1$ and $R_2$ may be bonded to form a $C_3$–$C_6$ alkylene group, an oxyalkylene group having a $C_3$–$C_6$ alkylene group or a thioalkylene group having $C_3$–$C_6$ alkylene group which may be substituted with a $C_1$–$C_3$ alkyl group, $R_3$ represents a hydrogen atom or CONRR', where R and R' represent a $C_1$–$C_6$ alkyl group, a $C_3$–$C_6$ alkenyl group, a $C_3$–$C_6$ alkynyl group, a cyanoalkyl group having a $C_1$–$C_6$ alkyl group or a phenyl group or benzyl group which may be substituted, or R and R' may be bonded to form a $C_3$–$C_6$ alkylene group, an oxyalkylene group having a $C_3$–$C_6$ alkylene group or a thioalkylene group, a $C_3$–$C_6$ alkylene which may be substituted with a $C_1$–$C_3$ alkyl group; $R_4$ represents

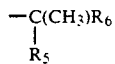

where $R_5$ represents a hydrogen atom, a lower alkyl group having 1 to 4 carbon atoms or a phenyl group, and $R_6$ represents a lower alkyl group having 1 to 6 carbon atoms, or $R_5$ and $R_6$ may be bonded to form a $C_2$–$C_7$ alkylene group, but $R_1$ and $R_2$ cannot be dialkylcarbamoyl groups at the same time.

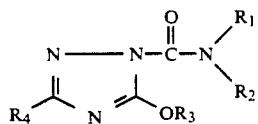

More specifically, the present invention relates to a triazole compound represented by the above formula (I), (hereinafter called the present compound) and an insecticidal composition for agriculture and horticulture or for a prevention of epidemics and having a high insecticidal activity against harmful insects of the Hemiptera, Diptera, Tylenchoida, and Aphelenchoida, families.

2. Description of the Related Art

The 3-t-butyl-1-(N,N-dimethylcarbamoyl)-1,2,4-triazole type compounds exhibiting insecticidal activities are known, as disclosed, for example, in Japanese Unexamined Patent Publications (Kokai) Nos. 52-122624, 52-122625, 55-38387, and 62-70365.

These compounds, however, do not have a satisfactory insecticidal spectrum and insecticidal performance. Particularly, it should be noted that the effect is not practically sufficient, or when the efficacy is high, a practical application has not been made for reasons such as damage due to chemicals. Further, the 5-position substituents of the triazoles are alkylthio, alkylthioalkylthio, and alkoxycarbonylalkylthio groups, which are entirely different from the $OR_3$ wherein $R_3$ is as defined above, which is the 5-position substituent of the present compound.

SUMMARY OF THE INVENTION

Accordingly, the objects of the present invention are to eliminate the above-mentioned disadvantages of the prior art and to provide a novel compound among 3-t-butyl-1-(N,N-dimethylcarbamoyl)-1,2,4-triazole compounds having a superior insecticidal spectrum and insecticidal performance.

Another object of the present invention is to provide a novel insecticide which has extremely high insecticidal activities against Hemiptera, Diptera, Tylenchoida, and Aphelenchoida, and has no adverse affects on crops.

Other objects and advantages of the present invention will be apparent from the following description.

In accordance with the present invention, there is provided a compound having the above-mentioned formula (I).

In accordance with the present invention, there is also provided an insecticide composition containing an insecticidal effective amount of the compound (I) as an active ingredient, and a carrier therefor.

DESCRIPTION OF THE PREFERRED EMBODIMENTS

After intensive studies were made to solve the above-mentioned problem, it was surprisingly found that the compound represented by the above formula (I) has a superior insecticidal spectrum and insecticidal performance, particularly an extremely high insecticidal activity against Hemiptera, Diptera, Tylenchoida, Aphelenchoida, and exhibits substantially no chemical damage to crops.

The present compound is a novel compound not found in known literature. The $R_1$ to $R_6$ and R and R' in the formula (I) are as defined above, and preferably $R_1$ and $R_2$ are each a methyl group, and $R_4$ is a t-butyl group or 1-methyl-cyclopropyl group.

Representative compounds of the compounds of the present invention are exemplified in Table 1.

The NMR values in the Table were measured at 60 MHz in deutero-chloroform with tetramethylsilane as the standard substance. The symbols s, d, tr, q, m indicate that the respective peak patterns are singlet, doublet, triplet, quartet, and multiplet, and br indicates a broad peak pattern.

The following descriptions are shown by the compound Nos. in the Table.

TABLE 1

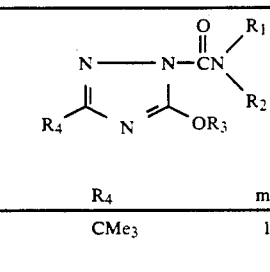

| Compound No | R₁ | R₂ | R₃ | R₄ | m.p. (°C.) | ¹H-NMR |
|---|---|---|---|---|---|---|
| 1 | Me | Me | $\overset{O}{\underset{\|}{C}}NMe_2$ | CMe₃ | 103-103.5 | δ1.3(s, 9H, t-Bu), δ2.95(s, 3H, NMe), δ3.05(s, 9H, NMe, NMe₂) |
| 2 | Et | Et | $\overset{O}{\underset{\|}{C}}NMe_2$ | CMe₃ | 110-111 | 1.25(t, J=6Hz, 6H, Me₂), δ1.35 (s, 9H, t-Bu), δ2.95(s, 3H, NMe), δ3.05(s, 3H, NMe), δ3.4(q, J=6Hz, 4H, (NCH₂—)₂) |
| 3 | Me | Me | $\overset{O}{\underset{\|}{C}}NEt_2$ | CMe₃ | 113-114 | δ1.1-1.3(m, tH, Me₂), δ1.35(s, 9H, t-Bu), δ3.05(s, 6H, NMe₂), δ3.2-3.6(m, 4H, (NCH₂—)₂) |
| 4 | Et | Et | $\overset{O}{\underset{\|}{C}}NEt_2$ | CMe₃ | 100-102 | δ1.1-1.5(m, 12H, Me₄), δ1.35(s, 9H, t-Bu), δ3.1-3.7(m, 8H, (NCH₂—)₄) |
| 5 | Me | Me | H | CMe₃ | 155-156 | δ1.3(s, 9H, t-Bu), δ3.1(s, 6H, NMe₂), δ12.1(br, s, 1H, OH) |
| 6 | Et | Et | H | CMe₃ | 106-107 | δ1.25(t, J=6Hz, 6H, Me₂), δ1.3 (s, 9H, t-Bu), δ3.4(q, J=6Hz, 4H, (NCH₂—)₂), δ11.7(br, s, 1H, OH) |
| 7 | H | Me | H | CMe₃ | 207-212 | δ1.3(s, 9H, t-Bu), δ2.95(d, J= 5Hz, 3H, NMe), δ7.7(br, s, 1H, NH) |
| 8 | H | n-Bu | H | CMe₃ | 152-154 | δ1.0(m, 3H, Me), δ1.2-1.8(m, 4H, (CH₂)₂), δ1.3(s, 9H, t-Bu), δ3.4(q, J=6Hz, 2H, NCH₂—), δ7.8(br, s, 1H, NH) |
| 9 | Me | $\overset{O}{\underset{\|}{C}}NMe_2$ | $\overset{O}{\underset{\|}{C}}NMe_2$ | CMe₃ | 111-113 | δ1.3(s, 9H, t-Bu), δ2.95(s, 6H, NMe₂), δ3.0(s, 3H, NMe), δ3.05(s, 3H, NMe), δ3.15(s, 3H, NMe) |
| 10 | Me | Me | $\overset{OMe}{\underset{\|}{C}}NEt$ (with ‖) | CMe₃ | 112-113 | δ1.05-1.4(m, 3H, Me), δ1.35(s, 9H, t-Bu), δ2.95, 3.05(s, 3H, NMe), δ3.05(s, 6H, NMe₂), δ3.1-3.6(m, 2H, NCH₂—) |
| 11 | Me | Me | $\overset{OMe}{\underset{\|}{C}}NnBu$ | CMe₃ | oil | δ0.95(m, 3H, Me), δ1.1-1.8(m, 4H, —CH₂—CH₂—), δ1.35(s, 9H, t-Bu), δ2.95, 3.05(s, 3H, NMe), δ3.05(s, 6H, NMe₂), δ3.1-3.5(m, 2H NCH₂—) |
| 12 | Me | Me | $\overset{O}{\underset{\|}{C}}N(isoPr)_2$ | CMe₃ | 89-90 | δ1.2, 1.3(s, 12H, Me₄), δ1.3(s, 9H, t-Bu), δ3.0(s, 6H, NMe₂), δ3.5-4.3 (m, 2H, (NCH)₂) |
| 13 | Me | Me | 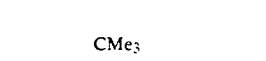 | CMe₃ | 121-122 | δ1.35(s, 9H, t-Bu), δ1.7-2.1(m, 4H, —CH₂—CH₂—), δ3.05(s, 6H, NMe₂), δ3.2-3.8(m, 4H, —CH₂NCH₂—) |
| 14 | Me | Me | 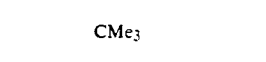 | CMe₃ | 95-96 | δ1.35(s, 9H, t-Bu), δ1.5-1.8(m, 6H, (CH₂)₃), δ3.05(s, 6H NMe₂), δ3.3-3.8(m, 4H, —CH₂NCH₂—) |
| 15 | Me | Me | 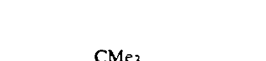 | CMe₃ | 96-98 | δ1.35(s, 9H, t-Bu), δ3.05(s, 6H, NMe₂), δ3.3-3.9(m, 8H, morpholine H) |
| 16 | Me | Me | 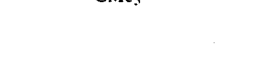 | CMe₃ | 78-79 | δ1.35(s, 9H, t-Bu), δ2.85, 3.00(s, 3H, NMe), δ3.05(s, 6H, NMe₂), δ4.45, 4.55(s, 2H, NCH₂—), δ7.1-7.3(m, 5H, PhH) |

TABLE 1-continued $$\underset{R_4}{\overset{N-N-\overset{O}{\overset{\|}{C}}N\overset{R_1}{\underset{R_2}{<}}}{\underset{N}{\parallel}\underset{OR_3}{\parallel}}}$$

| Compound No | R₁ | R₂ | R₃ | R₄ | m.p. (°C.) | ¹H-NMR |
|---|---|---|---|---|---|---|
| 17 | Me | Me | OMe<br>‖ ‖<br>CN—Ph | CMe₃ | oil | δ1.3(s, 9H, t-Bu), δ3.05(s, 6H, NMe₂), δ3.3(br, s, 3H, NMe), δ7.2 (br, s, 5H, NPhH) |
| 18 | Me | Me | OMe<br>‖ ‖<br>CN-n-Pr | CMe₃ | 72–73 | δ0.9(t, J=7Hz, 3H, Me), δ1.3(s, 9H, t-Bu), δ1.4–1.9(m, 2H, —CH₂—), δ2.9, 3.05(s, 3H, NMe), δ3.05(s, 6H, NMe₂), δ3.1–3.5(m, 2H, NCH₂—) |
| 19 | Me | Me | OMe<br>‖ ‖<br>CNCH₂CH=CH₂ | CMe₃ | 73–74 | δ1.35(s, 9H, t-Bu), δ2.9, 3.05(s, 3H, NMe), δ3.05(s, 6H, NMe₂), δ3.7–4.0(m, 2H, NCH₂—), δ4.8–5.8(m, 3H, —CH=CH₂) |
| 20 | Me | Me | OMe<br>‖ ‖<br>CNCH₂C≡CH | CMe₃ | 121–122 | δ1.35(s, 9H, t-Bu), δ2.2–2.4(m, 1H, —C≡CH), δ3.05(s, 6H, NMe₂), δ3.05, 3.15(s, 3H, NMe), δ4.0–4.3 (m, 2H, NCH₂—) |
| 21 | Me | Me | O<br>‖<br>CN(n-Pr)₂ | CMe₃ | oil | δ0.7–1.2(m, 6H, Me₂), δ1.35(s, 9H, t-Bu), δ1.4–2.0(m, 4H, (—CH₂—)₂), δ3.05(s, 6H, NMe₂), δ3.0–3.5(m, 4H, N(CH₂—)₂) |
| 22 | Me | Me | O<br>‖<br>CN(CH₂CH=CH₂)₂ | CMe₃ | 68–69 | δ1.35(s, 9H, t-Bu), δ3.05(s, 6H, NMe₂), δ3.7–4.1(m, 4H, N(CH₂—)₂), δ4.9–6.0(m, 6H, (—CH=CH₂)₂) |
| 23 | Me | Me | OMe<br>‖ ‖<br>CN-t-Bu | CMe₃ | 111–113 | δ1.35(s, 9H, t-Bu), δ1.4(s, 9H, N-t-Bu), δ3.05(s, 9H, NMe, NMe₂) |
| 24 | Me | Me | O<br>‖<br>CN(CH₂C≡CH)₂ | CMe₃ | 84–85 | 1.35(s, 9H, t-Bu), δ2.3–2.5(m, 2H, (—C≡CH)₂), δ3.05(s, 6H, NMe₂), δ4.1–4.5(m, 4H, N(CH₂—)₂) |
| 25 | Me | Me | O<br>‖<br>CN (CH₂)₆ | CMe₃ | 89–90 | δ1.35(s 9H, t-Bu), δ1.5–2.0(m, 8H, (—CH₂—)₄), δ3.05(s, 6H, NMe₂), δ3.2–3.7(m, 4H, N(CH₂—)₂) |
| 26 | Me | Me | O<br>‖<br>CN⟨ ⟩S | CMe₃ | 107–109 | δ1.35(s, 9H, t-Bu), δ3.05(s, 6H, NMe₂), δ2.9–3.2(m, 2H, —SCH₂—), δ3.5–4.0(m, 2H, NCH₂—), δ4.3–4.7 (m, 2H, NCH₂—) |
| 27 | Me | Me | OMe<br>‖ ‖<br>CN(CH₂)₂CN | CMe₃ | 89–91 | δ1.35(s, 9H, t-Bu), δ2.5–3.0(m 2H, —CH₂CN), δ3.05(s, 6H, NMe₂), δ3.05, 3.15(s, 3H, NMe), δ3.4–3.8 (m, 2H, NCH₂—) |
| 28 | n-Pr | n-Pr | O<br>‖<br>CNMe₂ | CMe₃ | 69–70 | δ0.7–1.1(m, 6H, Me₂), δ1.3(s, 9H, t-Bu), δ1.4–2.1(m, 4H, (—CH₂—)₂), δ2.95, 3.05(s, 6H, NMe₂), δ3.0–3.5 (m, 4H, N(CH₂—)₂) |
| 29 | n-Pr | n-Pr | O<br>‖<br>CN(n-Pr)₂ | CMe₃ | oil | δ0.7–1.2(m, 12H, Me₄), δ1.3(s, 9H, t-Bu), δ1.4–2.1(m, 8H, (—CH₂—)₄), δ2.8–3.5(m, 8H, N(CH₂—)₂, N(CH₂—)₂) |
| 30 | Me | Et | OMe<br>‖ ‖<br>CN—Et | CMe₃ | 103–104 | δ1.0–1.9(m, 6H, Me₂), δ1.35(s, 9H, t-Bu), δ2.8–3.7(m, 10H, NMe₂, N(CH₂—)₂) |

TABLE 1-continued

| Compound No | R₁ | R₂ | R₃ | R₄ | m.p. (°C.) | ¹H-NMR |
|---|---|---|---|---|---|---|
| 31 | Me | Me | 3-methyl-piperidin-1-yl carbonyl (O=C-N piperidine with Me at 3-position) | CMe₃ | 99-100 | δ0.9(d, J=6Hz, 3H, Me), δ1.3(s, 9H, t-Bu), δ1.5-2.1(m, 5H, —(CH₂)₂CH—), δ3.05(s, 6H, NMe₂), δ2.3-3.0, 3.7-4.3(m, 4H, N(CH₂—)₂) |
| 32 | Me | Me | 4-methyl-piperidin-1-yl carbonyl | CMe₃ | 109-110 | δ0.9-1.0(m, 3H, Me), δ1.3(s, 9H, t-Bu), δ1.3-1.9(m, 5H, —CH₂CHCH₂—), δ3.05(s, 6H, NMe₂), δ2.6-3.3, 3.8-4.4(m, 4H, N(CH₂—)₂) |
| 33 | Me | Me | 2-methyl-piperidin-1-yl carbonyl | CMe₃ | 90-91 | δ1.2-1.3(m, 3H, Me), δ1.3(s, 9H, t-Bu), δ1.4-1.9(m, 6H, (—CH₂—)₃), δ3.05(s, 6H, NMe₂), δ2.7-4.7(m, 3H, —CHNCH₂—) |
| 34 | Me | Me | 2,6-dimethyl-morpholin-4-yl carbonyl | CMe₃ | 82-83 | δ1.1-1.3(m, 6H, Me₂), δ1.3(s, 9H, t-Bu), δ3.05(s, 6H, NMe₂), δ2.5-4.2(m, 6H, N(CH₂CH—)₂O) |
| 35 | —(CH₂)₄— | | O=C-NMe₂ | CMe₃ | 102-103 | δ1.3(s, 9H, t-Bu), δ1.8-2.1(m, 4H, (—CH₂—)₂), δ2.95, 3.05(s, 6H, NMe₂), δ3.3-3.9(m, 4H, N(CH₂—)₂) |
| 36 | —(CH₂)₄— | | piperidin-1-yl carbonyl | CMe₃ | 122-123 | δ1.35(s, 9H, t-Bu), δ1.8-2.1(m, 8H, (—CH₂—)₄), δ3.3-3.9(m, 8H, N(CH₂—)₂, N(CH₂—)₂) |
| 37 | Me | Me | O=C-NMe₂ | CEt(Me)₂ | 74-75 | δ0.8(t, J=7Hz, 3H, Me), δ1.3(s, 6H, Me₂), δ1.7(q, J=7Hz, 2H, —CH₂—), δ2.95, 3.05(s, 6H, NMe₂), δ3.05(s, 6H, NMe₂) |
| 38 | Me | Me | OMe, O=C-N-Et | CEt(Me)₂ | 76-77 | δ0.8(t, J=7Hz, 3H, Me), δ1.0-1.4(m, 3H, Me), δ1.3(s, 6H, Me₂), δ1.7(q, J=7Hz, 2H, —CH₂—), δ2.95, 3.05(s, 3H, NMe), δ3.05(s, 6H, NMe₂), δ3.2-3.5(m, 2H, NCH₂—) |
| 39 | Me | Me | OMe, O=C-N-CH₂C≡CH | CEt(Me)₂ | 75-76 | δ0.8(t, J=7Hz, 3H, Me), δ1.3(s, 6H, Me₂), δ1.7(q, J=7Hz, 2H, —CH₂—), δ2.2-2.4(m, 1H, C≡CH), δ3.05(s, 6H, NMe₂), δ3.05, 3.1(s, 3H, NMe), δ4.0-4.3(m, 2H, NCH₂—) |
| 40 | Me | Me | pyrrolidin-1-yl carbonyl | CEt(Me)₂ | 107-108 | δ0.8(t, J=7Hz, 3H, Me), δ1.3(s, 6H, Me₂), δ1.5-2.1(m, 6H, —CH₂—, (—CH₂—)₂), δ3.05(s, 6H, NMe₂), δ3.2-3.7(m, 4H, N(CH₂—)₂) |
| 41 | Me | Me | piperidin-1-yl carbonyl | CEt(Me)₂ | 90-91 | δ0.8(t, J=7Hz, 3H, Me), δ1.3(s, 6H, Me₂), δ1.5-1.9(m, 8H, —CH₂—, (—CH₂—)₃), δ3.05(s, 6H, NMe₂), δ3.2-3.7(m, 4H, N(CH₂—)₂) |

TABLE 1-continued $$\begin{array}{c} \text{structure with } R_1, R_2, R_3, R_4 \end{array}$$

| Compound No | R₁ | R₂ | R₃ | R₄ | m.p. (°C.) | ¹H-NMR |
|---|---|---|---|---|---|---|
| 42 | Me | Me | -C(O)N-piperidine (with Me) | Me-CEt-Me | 66-68 | δ0.8(t, J=7Hz, 3H, Me), δ1.2-1.3(m, 3H, Me), δ1.3(s, 6H, Me₂), δ1.5-1.9(m, 8H, —CH₂—, (—CH₂—)₃), δ3.05(s, 6H, NMe₂), δ2.7-4.7(m, 3H, —CHNCH₂—) |
| 43 | Me | Me | -C(O)N-morpholine | Me-CEt-Me | 73-74 | δ0.8(t, J=7Hz, 3H, Me), δ1.3(s, 6H, Me₂), δ1.7(q, J=7Hz, 2H, —CH₂—), δ3.1(s, 6H, NMe₂), δ3.3-3.9(m, 8H, N(—C₂H₄—)₂O) |
| 44 | Me | Me | -C(O)N-(2,6-diMe-morpholine) | Me-CEt-Me | 90-91 | δ0.8(t, J=7Hz, 3H, Me), δ1.15(d, J=6Hz, 6H, Me₂), δ1.3(s, 6H, Me₂), δ1.7(q, J=7Hz, 2H, —CH₂—), δ3.05(s, 6H, NMe₂), δ2.5-4.2(m, 6H, N(—CH₂CH—)₂O) |
| 45 | Me | Me | -C(O)N-thiomorpholine | Me-CEt-Me | 79-80 | δ0.8(t, J=7Hz, 3H, Me), δ1.3(s, 6H, Me₂), δ1.7(q, J=7Hz, 2H, —CH₂—), δ2.8-3.2(m, 2H, SCH₂—), δ3.05(s, 6H, NMe₂), δ3.6-4.1(m, 2H, NCH₂—), δ4.3-4.7(m, 2H, NCH₂—) |
| 46 | Me | Me | -C(O)NMe₂ | Me-C(Me)-Ph | 98-102 | δ1.75(s, 6H, Me₂), δ2.95, 3.05(s, 6H, NMe₂), δ3.05(s, 6H, NMe₂), δ7.2 (br. s, 5H, PhH) |
| 47 | Me | Me | -C(O)NMe₂ | 1-Me-cyc-Pr | 76-77.5 | δ0.6-1.0(m, 2H, cyc-Pr), δ1.0-1.4(m, 2H, cyc-Pr), δ1.45(s, 3H, Me), δ2.95(s, 3H, NMe), 3.10(s, 9H, NMe₂, NMe₂) |
| 48 | Me | Me | -OMe, -C(O)NCH₂C≡CH | 1-Me-cyc-Pr | 94-95 | δ0.6-1.0(m, 2H, cyc-Pr), δ1.0-1.4(m, 2H, cyc-Pr), δ1.45(s, 3H, Me), δ2.2-2.4(m, 1H, C≡CH), δ3.05 (s, 9H, NMe, NMe₂), δ4.0-4.3(m, 2H, NCH₂) |
| 49 | Me | Me | -C(O)N-morpholine | 1-Me-cyc-Pr | oil | δ0.6-1.0(m 2H, cyc-Pr), δ1.0-1.4(m, 2H, cyc-Pr), δ1.45(s, 3H, Me), δ3.05(s, 6H, NMe₂), δ3.3-3.9(m, 8H, morpholine H) |
| 50 | Me | Me | -C(O)N-thiomorpholine | 1-Me-cyc-Pr | 89-91 | δ0.6-1.0(m, 2H cyc-Pr), δ1.0-1.4 (m, 2H, cyc-Pr), δ1.45(s, 3H, Me), δ3.05(s, 6H, NMe₂), δ2.9-3.2(m, 2H, SCH₂), δ3.6-4.0(m, 2H, NCH₂), δ4.4-4.7(m, 2H, NCH₂) |
| 51 | Me | Me | -C(O)N-(2-Me-piperidine) | 1-Me-cyc-Pr | 64-65 | δ0.6-1.0(m, 2H, cyc-Pr), δ1.0-1.5(m, 5H, cyc-Pr, Me), δ1.45(s, 3H, Me), δ1.4-1.9(m, 6H, (CH₂)₃), δ3.05(s, 6H, NMe₂), δ2.7-4.7(m, 3H, CHNCH₂) |
| 52 | Me | Me | -C(O)N-(2,6-diMe-morpholine) | 1-Me-cyc-Pr | oil | δ0.6-1.0(m, 2H, cyc-Pr), δ1.0-1.4(m, 8H, cyc-Pr, Me₂), δ1.45(s, 3H, Me), δ3.05(s, 6H, NMe₂), δ2.2-4.2(m, 6H, morpholine H) |

TABLE 1-continued

Structure:

$$\underset{R_4}{\overset{N-\!\!-\!\!-N-\overset{\displaystyle O}{\overset{\|}{C}}N\!\!\begin{array}{l}R_1\\R_2\end{array}}{\|\qquad\quad}}\underset{N}{\diagup}\overset{\diagdown}{OR_3}$$

| Compound No | $R_1$ | $R_2$ | $R_3$ | $R_4$ | m.p. (°C.) | $^1$H-NMR |
|---|---|---|---|---|---|---|
| 53 | Me | Me | (O=CN-piperidinyl) | 1-Me-cyc-Pr | 88-90 | δ0.6-1.0(m, 2H, cyc-Pr), δ1.0-1.4(m, 2H, cyc-Pr), δ1.45(s, 3H, Me), δ1.7-2.1(m, 4H, CH$_2$CH$_2$), δ3.05(s, 6H, NMe$_2$), δ3.2-3.8(m, 4H, CH$_2$NCH$_2$) |
| 54 | Me | Me | CNMe$_2$ (C=O) | 1-Me-cyc-Hex | oil | δ1.25(s, 3H, Me), δ1.2-2.5(m, 10H, cyc-Hex), δ2.95(s, 3H, NMe), δ3.05(s, 9H, NMe, NMe$_2$) |
| 55 | Me | Me | CNMe$_2$ (C=O) | sec-Bu | oil | δ0.85(t, J=7Hz, 3H, Me), δ1.25 (d, J=7Hz 3H, Me), δ1.3-2.0(m, 2H, CH$_2$), δ2.95(s, 3H, NMe), δ3.05 (s, 9H, NMe, NMe$_2$), δ2.9-3.3(m, 1H, CH) |
| 56 | Me | Me | CNMe$_2$ (C=O) | cyc-Hex | oil | δ1.0-2.3(m, 10H, cyc-Hex), δ2.95 (s, 3H, NMe), δ3.05(s, 9H, NMe, NMe$_2$), δ2.8-3.3(m, 1H, CH) |
| 57 | Me | Me | CNMe$_2$ (C=O) | iso-Pr | oil | δ1.30(d, J=7Hz, 6H, Me$_2$), δ2.95 (s, 3H, NMe), δ3.05(s, 9H, NMe, NMe$_2$), δ3.0-3.5(m, 1H, CH) |

The methods of preparing the compounds of the present invention are now described.

The compounds represented by the formula (I) ($R_3$=H) can be synthesized by reacting 3-t-1H-1,2,4-triazole-5-one with alkylcarbamoyl chloride represented by the formula (II) (wherein $R_1$ and $R_2$ represent lower alkyls) in a solvent in the presence of a base.

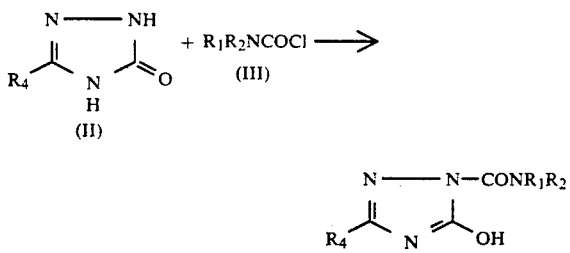

Further, the reaction product can be reacted with the same or a different kind of carbamoyl chloride, to be converted into a carbamic acid ester.

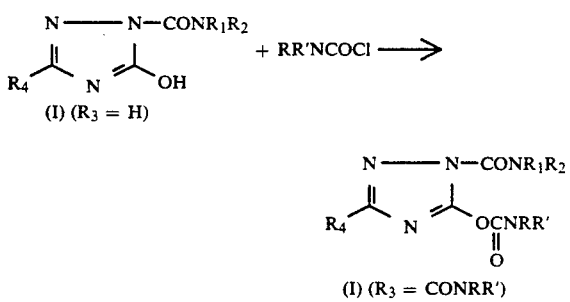

Also, the compound of (I) of $R_3$=CONR$_1$R$_2$ can be synthesized from the starting material of (II) in one step, by using 2 to 3 equivalents of (III).

As the solvent to be used in the above synthetic method, there may be included, for example, ethers such as dioxane, tetrahydrofuran, and diethyl ether; esters such as ethyl acetate; ketones such as acetone and methyl ethyl ketone; halogenated hydrocarbons such as methylene chloride and chloroform; and aromatic hydrocarbons such as benzene, toluene, and xylene.

As the base to be added, there may be included tertiary amines such as triethylamine and 4-N,N-dimethylaminopyridine; pyridines or alkali hydroxides such as sodium hydroxide and potassium hydroxide; and alkali carbonates such as sodium carbonate, potassium carbonate, and sodium hydrogen carbonate.

Synthesis Examples of the present compound are now shown, but the present invention is not limited thereto.

SYNTHESIS EXAMPLE 1

Synthesis of (3-tert-butyl-N,N-dimethylcarbamoyl-1,2,4-triazol-5-yl)-N',N'-dimethylcarbamate 1-1. Synthesis of 3-tert-butyl-1H-1,2,4-triazole-5-one To 111.5 g (1 mole) of semicarbazide hydrochloride were added an aqueous sodium hydroxide solution of 80 g (2 moles) of sodium hydroxide dissolved in 300 ml of water, and 300 ml of 1,4-dioxane. After the semicarbazide hydrochloride was completely dissolved, the reaction mixture was cooled to make the temperature of the solution 20° C. or lower, and to the solution was dropwise added 121 g (1 mole) of trimethylacetyl chloride while stirring, to maintain the reaction temperature at 20° C. or lower. After completion of the dropwise addition, the reaction mixture was returned to room temperature, and stirring was continued for an additional 2 hours. The white precipitates of trimethylacetyl semicarbazide formed were collected by filtration, washed with water, and dried.

To the white powder of the trimethylacetyl semicarbazide obtained was added 1500 ml of a 5% aqueous potassium hydroxide solution, and the mixture was heated to 100° C. while stirring. After the contents were completely dissolved, the solution was further heated at 100° C. for one hour, and the reaction mixture then cooled and neutralized by an addition of conc. sulfuric acid. The white precipitates formed were collected by filtration, washed with water, and then dried under a reduced pressure to yield 64 g of white powder of 3-tert-butyl-1H-1,2,4-triazole-5-one. (yield 45%)

1-2. Synthesis of (3-tert-butyl-1-N,N-dimethylcarbamoyl-1,2,4-triazol-5-yl)-N',N'-dimethylcarbamate To a mixture of 14.1 g (0.1 mole) of 3-tert-butyl-1H-1,2,4-triazol-5-one, 30.0 g (0.3 mole) of triethylamine, and 1.2 g (0.01 mole) of 4-N,N-dimethylaminopyridine was added 150 ml of tetrahydrofuran. Then 28.0 g (0.26 mole) of N,N-dimethylcarbamoyl chloride was added to the mixture while stirring, and the mixture was heated under reflux for 6 hours. The reaction mixture was then cooled to room temperature, and the triethylamine hydrochloride removed by filtration. After the filtrate portion was concentrated under a reduced pressure, water was added, and the mixture extracted with methylene chloride. The organic extract was dried over anhydrous sodium sulfate, and then concentrated under a reduced pressure. The product obtained was subjected to silica gel column chromatography, and eluted with a 1:1 solvent mixture of acetone and methylene chloride to obtain 24.7 g of colorless crystals of (3-tert-butyl-1-N,N-dimethylcarbamoyl, 1,2,4-triazol-5-yl)-N',N'-dimethylcarbamate (yield 87%).

SYNTHESIS EXAMPLE 2

Synthesis of (3-tert-butyl-1-N,N-dimethylcarbamoyl-1,2,4-triazol-5-yl)-N',N'-diethylcarbamate

2-1. Synthesis of 3-tert-butyl-1-N,N-dimethylcarbamoyl-5-hydroxy-1,2,4-triazole Preparation Method 1

To a mixture of 7.05 g (0.05 mole) of 3-tert-butyl-1H-1,2,4-triazole-5-one, 7.5 g (0.075 mole) of triethylamine, and 0.31 g (0.0025 mole) of 4-N,N-dimethylaminopyridine was added 100 ml of tetrahydrofuran. The mixture was completely dissolved by heating to 70° C. with stirring, and to the solution was added 5.9 g (0.055 mole) of N,N-dimethylcarbamoyl chloride, and the reaction was further carried out at 70° C. for 45 minutes. After the reaction mixture was concentrated under a reduced pressure, water was added, the mixture was extracted with methylene chloride, and the organic extract was dried over anhydrous sodium sulfate and then concentrated under a reduced pressure. The white solid obtained was further recrystallized from ethyl acetate to yield 3.6 g of white crystals of 3-tert-butyl-1-N,N-dimethylcarbamoyl-5-hydroxy-1,2,4-triazole (yield 34%).

Preparation Method 2

To 24.0 g (0.085 mole) of the (3-tert-butyl-1-N,N-dimethylcarbamoyl-1,2,4-triazol-5-yl)-N',N'-dimethylcarbamate obtained in Example 1 was added 200 ml of tetrahydrofuran, to dissolve the compound, to the solution was added 25 ml of conc. sulfuric acid, and the mixture was left to stand for 2 hours. The solution was then poured into ice-water and neutralized with an aqueous 4N sodium hydroxide solution. The aqueous solution was extracted with methylene chloride, and the organic extract obtained was dried over anhydrous sodium sulfate, followed by concentration under a reduced pressure. The white solid obtained was washed with n-hexane to give 15.2 g of white crystals of 3-tert-butyl-1-N,N-dimethylcarbamoyl-5-hydroxy-1,2,4-triazole. (yield 84%).

2-2. Synthesis of (3-tert-butyl-1-N,N-dimethylcarbamoyl-1,2,4-triazol-5-yl)-N',N'-diethylcarbamate To a mixture of 3.18 g (0.015 mole) of 3-tert-butyl-1-N,N-dimethylcarbamoyl-5-hydroxy-1,2,4-triazole, 3.0 g (0.03 mole) of triethylamine, and 0.18 g (0.0015 mole) of 4-N,N-dimethylaminopyridine was added 50 ml of tetrahydrofuran. To the mixed solution was added 4.1 g (0.03 mole) of N,N-diethylcarbamoyl chloride, and the mixture was heated under reflux for 6 hours, and after concentration of the reaction mixture under a reduced pressure, water was added and the mixture was extracted with methylene chloride.

The organic extract was dried over anhydrous sodium sulfate, and then concentrated under a reduced pressure. The pale yellow solid obtained was subjected to silica gel column chromatography and extracted with ethyl acetate to give a white solid of (3-tert-butyl-1-N,N-dimethylcarbamoyl-1,2,4-triazol-5-yl)-N',N'-diethylcarbamate. This was further recrystallized from ethyl acetate to give 3.5 g of colorless crystals of the desired product. (yield 75%)

The compound was further recrystallized from n-hexane to give colorless needles, and by an X-ray crystal structure analysis thereof, the compound was confirmed to have the title structure.

SYNTHESIS EXAMPLE 3

Synthesis of 3-tert-butyl-1-N-methylcarbamoyl-5-hydroxy-1,2,4-triazole

To a mixture of 1.41 g (0.01 mole) of 3-tert-butyl-1H-1,2,4-triazole-5-one and 0.5 g of triethylamine was added 50 ml of tetrahydrofuran, to the mixture was added 2.28 g (0.04 mole) of methylisocyanate while stirring, and the reaction was carried out at 60° C. for 2 hours. By concentration of the reaction mixture under a reduced pressure a white powder was obtained, which was washed with n-hexane to give 1.6 g of white powder of 3-tert-butyl-1-N-methylcarbamoyl-5-hydroxy-1,2,4-triazole. (yield 81%)

SYNTHESIS EXAMPLE 4

Synthesis of (3-tert-butyl-1-pyrrolidinecarbonyl-1,2,4-triazol-5-yl)-pyrrolidinecarbamate To a mixture of 2.82 g (0.02 mole) of 3-tert-butyl-1H-1,2,4-triazole-5-one, 6.00 g (0.06 mole) of triethylamine, and 0.25 g (0.002 mole) of 4-N,N-dimethylaminopyridine was added 50 ml of tetrahydrofuran, to this mixture was added 6.70 g (0.05 mole) of pyrrolidinecarbonyl chloride while stirring and, after heating under reflux for 3 hours, 1.30 g (0.01 mole) of pyrrolidinecarbonyl chloride was added, and the mixture was heated under reflux for 11 hours. After concentration of the reaction mixture under a reduced pressure, water was added and the mixture was extracted with methylene chloride. The organic extract was dried over anhydrous sodium sulfate, and then concentrated under a reduced pressure. The product obtained extract was subjected to silica gel column chromatography and eluted with a 1:9 solvent mixture of acetone and methylene chloride to give 6.10 g of a white solid of 3-tert-butyl-1-pyrrolidinecarbonyl(1,2,4-triazol-5-yl)-pyrrolidinecarbamate. This was further washed with n-hexane to give 5.80 g of white powder. (yield 87%)

SYNTHESIS EXAMPLE 5

Synthesis of (3-tert-butyl-1-pyrrolidinecarbonyl-1,2,4-triazol-5-yl)-N',N'-dimethylcarbamate 5-1. Synthesis of 3-tert-butyl-1-pyrrolidinecarbonyl-5-hydroxy-1,2,4-triazole To 3.60 g (0.011 mole) of the 3-tert-butyl-1-pyrrolidinecarbonyl-(1,2,4-triazol-5-yl)-pyrrolidinecarbamate obtained in Synthesis Example 4 was added 50 ml of tetrahydrofuran, to dissolve the compound, to the solution was added 2 ml of conc. sulfuric acid at room temperature, and the mixture was left to stand for 2 hours. The solution was poured into ice-water, and neutralized with an aqueous 4N sodium hydroxide solution. The aqueous solution was extracted with methylene chloride, and the organic extract obtained was dried over anhydrous sodium sulfate, followed by concentration under a reduced pressure. The white solid obtained was washed with n-hexane to give 2.55 g of white powder of 3-tert-butyl-1-pyrrolidinecarbonyl-5-hydroxy-1,2,4-triazole. (yield 98%)

5-2. Synthesis of (3-tert-butyl-1-pyrrolidinecarbonyl-1,2,4-triazol-5-yl)-N',N'-dimethylcarbamate To a mixture of 1.90 g (0.008 mole) of 3-tert-butyl-1-pyrrolidinecarbonyl-5-hydroxy-1,2,4-triazole, 1.60 g (0.016 mole) of triethylamine, and 0.10 g (0.0008 mole) of 4-N,N-dimethylaminopyridine was added 30 ml of tetrahydrofuran.

Then to the mixed solution was added 1.08 g (0.01 mole) of N,N-dimethylcarbamoyl chloride, and the mixture was heated under reflux for 7 hours, and after concentration of the mixture under a reduced pressure, water was added and the mixture was extracted with methylene chloride. The organic extract was then dried over anhydrous sodium sulfate, and concentrated under a reduced pressure. The product obtained was subjected to silica gel column chromatography and eluted with a 1:9 solvent mixture of acetone and methylene chloride to give 2.00 g of colorless crystals of (3-tert-butyl-1-pyrrolidinecarbonyl-1,2,4-triazol-5-yl)-N',N'-dimethylcarbamate. (yield 81%)

SYNTHESIS EXAMPLE 6

Synthesis of (3-tert-butyl-1-N,N-dimethylcarbamoyl-1,2,4-triazol-5-yl)-(2-methylpiperidine)carbamate 6-1. Synthesis of 3-tert-butyl-1-N,N-dimethylcarbamoyl-5-hydroxy-1,2,4-triazole To a mixture of 50 g (0.36 mole) of 3-tert-butyl-1H-1,2,4-triazole-5-one, 43 g (0.43 mole) of triethylamine, and 1.0 g (0.008 mole) of 4-N,N-dimethylaminopyridine was added 500 ml of tetrahydrofuran. To the solution was added 41.9 g (0.39 mole) of N,N-dimethylcarbamoyl chloride while stirring, and the mixture was heated under reflux for 3 hours. The reaction mixture was left to cool to room temperature, the triethylamine hydrochloride was removed by filtration, to the solution was added 40 ml of conc. hydrochloric acid at room temperature, and the mixture was left to stand for 2 hours.

The solution was poured into ice-water, and then neutralized with an aqueous 4N sodium hydroxide solution. The aqueous solution was extracted with ethyl acetate and then methylene chloride, and the organic extracts obtained were combined and dried over anhydrous sodium sulfate. By concentration of the solution under a reduced pressure, a white solid was obtained. The white solid obtained was washed with n-hexane to give 70.3 g of white powder of 3-tert-butyl-1-N,N-dimethylcarbamoyl-5-hydroxy-1,2,4-triazole. (yield 93%)

6-2. Synthesis of (3-tert-butyl-1-N,N-dimethylcarbamoyl-1,2,4-triazol-5-yl)-(2-methylpiperidine)carbamate To a mixture of 3.18 g (0.015 mole) of 3-tert-butyl-1-N,N-dimethylcarbamoyl-5-hydroxy-1,2,4-triazole, 3.00 g (0.03 mole) of triethylamine, and 0.18 g (0.0015 mole) of 4-N,N-dimethylaminopyridine was added 50 ml of tetrahydrofuran.

To the mixed solution was added 2.90 g (0.018 mole) of 2-methylpiperidine-carbonyl chloride, and the mixture was heated under reflux for 5 hours, and after concentration of the mixture under a reduced pressure, water was added and the mixture was extracted with methylene chloride. The organic extract was dried over anhydrous sodium sulfate, and then concentrated under a reduced pressure. The product obtained was subjected to silica gel column chromatography and eluted with a 1:1 solvent mixture of ethyl acetate and n-hexane to give 3.90 g of colorless solid of 3-tert-butyl-1-N,N-dimethylcarbamoyl(1,2,4-triazol-5-yl)-(2-methylpiperidine)carbamate. (yield 77%)

SYNTHESIS EXAMPLE 7

Synthesis of (3-tert-amyl-1-N,N-dimethylcarbamoyl-1,2,4-triazol-5-yl)-N',N'-dimethylcarbamate 7-1. Synthesis of 3-tert-amyl-1H-1,2,4-triazole-5-one To 55.8 g (0.5 mole) of semicarbazide hydrochloride were added an aqueous sodium hydroxide solution of 40.0 g (1 mole) of sodium hydroxide dissolved in 150 ml of water and 150 ml of 1,4-dioxane. After the semicarbazide hydrochloride was completely dissolved, the reaction mixture was cooled to make the temperature of the solution 20° C. or lower, and to the solution was dropwise added 67.3 g (0.5 mole) of 2,2-dimethylbutyryl chloride while stirring, to maintain the reaction temperature at 20° C. or lower. After completion of the dropwise addition, the reaction mixture was returned to room temperature, and stirring was continued for an additional 8 hours.

Subsequently, to the solution was added a solution of 35 g (0.6 mole) of potassium hydroxide dissolved in 100 ml of water, and heating was continued at 100° C. for 3 hours while stirring. After completion of the heating, the reaction mixture was cooled and then neutralized by an addition of hydrochloric acid. The white precipitates formed were collected by filtration, washed with water, and then dried under a reduced pressure to give 30.0 g of white powder of 3-tert-amyl-1H-1,2,4-triazole-5-one. (yield 39%)

7-2. Synthesis of (3-tert-amyl-1-N,N-dimethylcarbamoyl-1,2,4-triazol-5-yl)-N',N'-dimethylcarbamate To a mixture of 1.80 g (0.011 mole) of 3-tert-amyl-1H-1,2,4-triazole-5-one, 4.00 g (0.04 mole) of triethylamine, and 0.12 g (0.001 mole) of 4-N,N-dimethylaminopyridine was added 50 ml of tetrahydrofuran. To the mixture was added 3.50 g (0.033 mole) of N,N-dimethylcarbamoyl chloride while stirring, and the mixture was heated under reflux for 3 hours. After the reaction mixture was concentrated under a reduced pressure, water was added, and the mixture then extracted with methylene chloride. The organic extract was dried over anhydrous sodium sulfate and then concentrated under a reduced pressure. The product obtained was subjected to silica gel column chromatography, and eluted with a 1:9 solvent mixture of acetone and methylene chloride to obtain 2.30 g of colorless needles of (3-tert-amyl-1-N,N-dimethylcarbamoyl-1,2,4-triazol-5-yl)-N',N'-dimethylcarbamate. (yield 66%)

SYNTHESIS EXAMPLE 8

Synthesis of 1-N,N-dimethylcarbamoyl-3-(1-methyl-1-phenylethyl)-(1,2,4-triazol-5-yl)-N',N'-dimethylcarbamate

8-1. Synthesis of 3-(1-methyl-1-phenylethyl)-1H-1,2,4-triazole-5-one

To 22.3 g (0.2 mole) of semicarbazide hydrochloride were added an aqueous sodium hydroxide solution of 16.0 g (0.4 mole) of sodium hydroxide dissolved in 60 ml of water and 60 ml of 1,4-dioxane. After the semicarbazide hydrochloride was completely dissolved, the reaction mixture was cooled to make the temperature of the solution 20° C. or lower, and to the solution was dropwise added 36.5 g (0.2 mole) of 2-methyl-2-phenylpropionyl chloride while stirring, to maintain the reaction temperature at 20° C. or lower. After completion of the dropwise addition, the reaction mixture was returned to room temperature, and stirring was continued for an additional 3 hours. The white precipitates of (2-methyl-2-phenylpropionyl) semicarbazide formed were collected by filtration, washed with water and dried.

To the white powder of (2-methyl-2-propionyl) semicarbazide obtained was added a solution of 11.2 g (0.2 mole) of potassium hydroxide solution dissolved in 200 ml of water and the mixture was heated to 100° C. while stirring. After the contents were completely dissolved, the solution was further heated at 100° C. for 4 hours, and after completion of the heating, the reaction mixture was cooled and then neutralized by an addition of conc. hydrochloric acid. The white precipitates formed were collected by filtration, washed with water, and then dried under a reduced pressure to give 12.8 g of white powder of 3-(1-methyl-1-phenylethyl)-1H-1,2,4-triazole-5-one. (yield 32%)

8-2. Synthesis of 1-N,N-dimethylcarbamoyl-3-(1-methyl-1-phenylethyl)-(1,2,4-triazol-5-yl)-N',N'-dimethylcarbamate To a mixture of 2.03 g (0.01 mole) of 3-(1-methyl-1-phenylethyl)-1H-1,2,4-triazol-5-one, 4.00 g (0.04 mole) of triethylamine, and 0.12 g (0.001 mole) of 4-N,N-dimethylaminopyridine was added 50 ml of tetrahydrofuran. To the mixture was added 3.50 g (0.033 mole) of N,N-dimethylcarbamoyl chloride while stirring, and the mixture was heated under reflux for 3 hours. After concentration of the reaction mixture under a reduced pressure, water was added, and the mixture then extracted with methylene chloride. The organic extract was dried over anhydrous sodium sulfate and then concentrated under a reduced pressure.

The product obtained was subjected to silica gel column chromatography, eluted with a 1:1 solvent mixture of ethyl acetate and n-hexane, and then with a 1:2 solvent mixture of the same solvents, and further, with only ethyl acetate, to obtain 1.40 g of a white solid of the desired product 1-N,N-dimethylcarbamoyl-3-(1-methyl-1-phenylethyl)-(1,2,4-triazol-5-yl)-N',N'-dimethylcarbamate. (yield 41%)

SYNTHESIS EXAMPLE 9

Synthesis of 1-N,N-dimethylcarbamoyl-3-(1-methylcyclopropyl)-(1,2,4-triazol-5-yl)-N',N'-dimethylcarbamate

9-1. Synthesis of 3-(1-methyl-1-cyclopropyl)-1H-1,2,4-triazole-5-one

To 55.8 g (0.5 mole) of semicarbazide hydrochloride were added an aqueous sodium hydroxide solution of 40.0 g (1 mole) of sodium hydroxide dissolved in 150 ml of water and 150 ml of 1,4-dioxane. After semicarbazide hydrochloride was completely dissolved, to the solution was dropwise added 59.3 g (0.5 mole) of 1-methylcyclopropanecarboxylic acid chloride while stirring the reaction mixture, to maintain the reaction temperature at 40° C. or lower. After completion of the dropwise addition, the reaction mixture was returned to room temperature, and stirring was continued for an additional 3 hours. The white precipitates of 1-methylcyclopropanecarbonyl semicarbazide formed were collected by filtration, washed with water and dried.

To the white powder of 1-methyl-cyclopropanecarbonyl semicarbazide obtained was added a solution of 28.0 g (0.5 mole) of potassium hydroxide dissolved in 400 ml of water, and the mixture was heated to 100° C. while stirring. After the contents were completely dissolved, the solution was further heated at 100° C. for 4 hours, and after completion of the heating, the reaction mixture was cooled and then neutralized by an addition of conc. hydrochloric acid. The white precipitates formed were collected by filtration, washed with water, and then dried under a reduced pressure to give 30.6 g of white powder of the desired product 3-(1-methylcyclopropyl)-1H-1,2,4-triazole-5-one. (yield 44%)

9-2. Synthesis of 1-N,N-dimethylcarbamoyl-3-(1-methylcyclopropyl)-(1,2,4-triazol-5-yl)-N',N'-dimethylcarbamate To a mixture of 2.09 g (0.015 mole) of 3-(1-methylcyclopropyl)-1H-1,2,4-triazol-5-one, 5.00 g (0.05 mole) of triethylamine, and 0.18 g (0.0015 mole) of 4-N,N-dimethylaminopyridine was added 50 ml of tetrahydrofuran. To the mixture was added 4.80 g (0.045 mole) of N,N-dimethylcarbamoyl chloride while stirring, the mixture was heated under reflux for 2.5 hours, and after concentration of the reaction mixture under a reduced pressure, water was added, and the mixture then extracted with methylene chloride. The organic extract was dried over anhydrous sodium sulfate and then concentrated under a reduced pressure. The product obtained was subjected to silica gel column chromatography, and eluted with ethyl acetate to obtain 3.90 g of white crystals of the desired product 1-N,N-dimethylcarbamoyl-3-(1-methylcyclopropyl)-(1,2,4-triazol-5-yl)-N',N'-dimethylcarbamate. (yield 93%)

The insecticidal composition of the present invention exhibits superior effects against Hemiptera such as aphids, etc., Diptera such as flies and mosquitoes, Tylenchoida such as root-knot nematode, and Aphelenchoida such as large thorn nematode. In the following, the names of harmful insects against which the composition has a high activity are exemplified, but the harmful insects against which the present compound is effective are not limited thereto.

As the insects, there may be included:
Coleoptera harmful insects, such as:
  *Anomala refocuprea;*
  *Callosobruchus chinemsis;*
  *Sitophilus zeavais;*
  *Epilachna vigintioctomaculata;*
  *Lissorhoptrum oryzophilus;*
Hemiptera harmful insects, such as:
  *Laodelphox striatellus;*
  *Nilaparvata lugens;*
  *Sogatella furcifera;*
  *Nephotettix cincticeps;*
  *Nezara amtennata;*
  *Trialeurodes vaporariorum;*
  *Unaspis yanoneusis;*
  *Aplris gossypii;*
  *Myzus persical;*
  *Aulacorthum solani;*
  *Rhopalosiphus pseudobrassicae;*
Diptera harmful insects, such as:
  *Musca domestica;*
  *Aedes aegypti;*
  *Culex pipiens;*
Orthoptera harmful insects such as:
  *Blatella germanica;*
  *Periplaneta americana;*
  *Locuota mioratoria;*
Isoptera harmful insects such as:
  *Copto termes formosawis;*
Lepidoptera harmful insects such as:
  *Pieris rapae;*
  *Plutella xylostella;*
  *Mamestra brassicae;*
  *Spondoptera litura;*
  *Heliothis virescens;*
  *Agrotis fucosa;*
  *Chilo suppressalis;* etc.

As the mites, there can be included, for example:
  *Tetranychus urticae;*
  *Panonychus citri;*
  *Aculops pelekassi;* etc.

The insecticide can be also used in the form of a single compound without the addition of other components, when practically applied, but to make it readily available as the control chemical, generally a carrier is formulated into a preparation and is diluted if necessary before use. When forming the insecticide of the present invention into a preparation, no special conditions need be met, and it can be prepared in any desired dosage form such as an emulsion, wettable agent, powder, or granules, etc., by conventionally well known methods for general agricultural chemicals. As the carrier, there may be included inorganic materials such as clays, talc, bentonite, calcium carbonate, diatomaceous earth, zeolite, and anhydrous silicic acid; vegetable organic materials such as wheat, starch, and crystalline cellulose; polymeric compounds such as petroleum resin, polyvinyl chloride, and polyalkylene glycol; urea; waxes; and so on. As the liquid carrier, various oils, organic solvents, and water may be included. Further, auxiliary agents required in the preparation, such as humectants, dispersing agents, anchoring agents, and extenders, can be used either alone or in combination, if necessary. As auxiliary agents used for such purposes as wetting, dispersing, extending, component stabilization, and rust prevention, etc., there may be included various surfactants, polymeric compounds such as gelatin, albumin, sodium alginate, methyl cellulose, carboxymethyl cellulose, polyvinyl alcohol, and xanthane gum, and other auxiliary agents. As surfactants, there may be included nonionic surfactants such as polymerized products of ethylene oxide with alkylphenol, higher alcohol, alkylnaphthol, higher fatty acid, fatty acid ester, and dialkylphosphoric acid amine; polymerized products of ethylene oxide and propylene oxide; anionic surfactants, including alkylsulfates such as sodium laurylsulfate; alkylsulfonates such as sodium 2-ethylhexylsulfonate; arylsulfonates such as sodium ligninsulfonate, sodium and dodecylbenzenesulfonate; and various cationic and amphoteric surfactants.

Also, by mixing the insecticide with other physiologically active substances, multi-purpose agricultural chemicals can be made. As the physiologically active substances, there are known insecticides and acaricides, and further, sterilizers, nematocides, herbicides, plant controllers, fertilizers, BT agents, nuclear polyhedrosis virus, and insect hormone agents. Specific examples of these physiologically active substances are set forth below.

Pyrethroid and pyrethroid complex compounds such as ethofenprox [2-(4-ethoxyphenyl)-2-methylpropyl-3-phenoxy-benzyl ether], fenvalerate [3-phenoxy-α-cyano-benzyl-α-isopropyl-4-chlorophenylacetate], permethrin [3-phenoxybenzyl-3-(2,2-dichlorovinyl)-2,2-dimethylcyclopropane-1-carboxylic acid ester], cypermethrin [3-phenoxy-α-cyanobenzyl-3-(2,2-dichlorovinyl)-2,2-dimethylcyclopropane-1-carboxylic acid ester], deltamethrin [3-phenoxy-α-cyanobenzyl-3-(2,2-dibromovinyl)-2,2-dimethylcyclopropane-1-carboxylic acid ester], or insectifuges, etc. Organic phosphorus type insecticides such as pyridafenthion [o,o-diethyl-o-(3-oxo-2N-phenyl-2H-pyridazin-6-yl)phosphorothioate], DDVP [o,o-dimethyl-o-(2,2-dichlorovinyl)phosphate], fenitrothion [o,o-dimetyl-o-(3-methyl-4-nitrophenyl)phosphorothioate], etc. Carbamate type insecticides such as NAC [1-naphthyl-N-methylcarbamate], MTMC [meta-tolyl-N-methylcarbamate], pyrimer [2-dimethylamino-5,6-dimethylpyrinidin-4-yl-dimethylcarbanate], etc. Integument formation inhibitors such as buprofezin [2-tert-butylimino-3-isopropyl-5-phenyl-3,4,5,6-tetrahydro-2H-1,3,5-thidiazine-4-one], CME134 [1-(3,5-dichloro-2,4-difluorophenyl)-3-(2,6-difluorobenzoyl)urea], etc. Fungicides such as phthalide [4,5,6,7-tetrachlorophthalide], IBP [S-benzyl-diisopropylphosphorothioate], EDDP [o-ethyl-diphenylphosphorodithioate], benomyl [methyl-1-(butylcaramoyl)-2-benzimidazolecarbamate], probenazole [3-allyloxy-1,2-benzisothiazole-1,1dioxide], isoprothiolane [diisopropyl-1,3-dithioran-2-ylidene malonate], tricyclazole [5-methyl-1,2,4-triazolo-(3,4-b)benzothiazole), etc. Acaricides such as kelthane [2,2,2-trichloro-1,1-bis(p-chlorophenylethanol], amitraz [3- methyl-1,5-bis(2,4-xylyl)(1,3,5-triazapenta-1,4-diene], tricyclohexyltin hydroxide, etc.

The ingredient component is included in the insecticidal composition of the present invention in an amount of preferably 0.001 to 95% by weight, more preferably 0.1 to 70% by weight.

Preparation Examples as insecticides of the present invention are now shown, but the present invention is not limited thereto.

PREPARATION EXAMPLE 1

Powder

Three parts by weight of the present compound, 10 parts by weight of Carplex #80 [White carbon, manufactured by Shionogi Seiyaku K.K.], and 87 parts by weight of clay were mixed and pulverized to obtain 100 parts of powder containing 3% by weight of the active ingredient.

PREPARATION EXAMPLE 2

Powder 0.5 part by weight of the present compound, 49.5 parts by weight of calcium carbonate, and 50 parts by weight of clay were mixed and pulverized to obtain 100 parts by weight of powder containing 0.5% by weight of the active ingredient.

PREPARATION EXAMPLE 3

Wettable agent 50 parts by weight of the present compound, 5 parts by weight of Sorpol [surfactant, manufactured by Toho Kagaku K.K.], and 45 parts by weight of Radiolite [calcined diatomaceous earth, manufactured by Showa Kagaku K.K.] were uniformly pulverized and mixed to obtain 100 parts by weight of wettable agent containing 50% by weight of the active ingredient.

PREPARATION EXAMPLE 4

Wettable agent 10 parts by weight of the present compound, 10 parts by weight of Carplex #80 [white carbon, manufactured by Shionogi Seiyaku K.K.], 3 parts by weight of Emal 10 [surfactant, manufactured by Kao K.K.], and 77 parts by weight of clay were uniformly mixed and pulverized to obtain 100 parts by weight of a wettable agent containing 10% by weight of the active ingredient.

PREPARATION EXAMPLE 5

Granules

One part by weight of the present compound, 2 parts by weight of sodium dodecylbenzenesulfonate, 1 part by weight of sodium ligninsulfonate, 25 parts by weight of talc, and 71 parts by weight of bentonite were uniformly mixed, kneaded with an addition of water, and then granulated by an extrusion granulator, followed by drying, to obtain 100 parts by weight of granules containing 1% by weight of the active ingredient.

PREPARATION EXAMPLE 6

Granules

Three parts by weight of the present compound, 3 parts by weight of carboxymethyl cellulose, 2 parts by weight of sodium ligninsulfonate, and 92 parts by weight of clay were uniformly mixed, kneaded with an addition of water, and then granulated by an extrusion granulator, followed by drying, to obtain 100 parts by weight of granules containing 3% by weight of the active ingredient.

PREPARATION EXAMPLE 7

Mixed wettable agent 20 parts by weight of the present compound, 10 parts by weight of ethofenprox, 5 parts by weight of Sorpol [surfactant, manufactured by Toho Kagaku K.K.], and 65 parts by weight of Radiolite [calcined diatomaceous earth, manufactured by Showa Kagaju K.K.] were uniformly mixed to obtain 100 parts by weight of a mixed wettable agent containing 20% by weight of the present compound and 10% by weight of ethofenprox, respectively, as the active ingredients.

The control effect of the present compound is now described in detail with reference to biological test examples.

TEST EXAMPLE 1

Insecticidal effect against *Nephotettix cincticeps*

The wettable agent of the present compound formed into a preparation was adjusted to 500 ppm of the active ingredient by dilution with water. The chemical solution was sprayed on rice seedlings in the 3-4 leaf stage and planted in a pot, and after air drying, covered by an acrylic resin cylinder. Into this cylinder was freed 10 female adult insects of *Nephotettix cincticeps*, and after 2 days, the numbers of dead and alive insects were examined to calculate the mortality ratio. The results are shown in Table 2.

TABLE 2

| Compound No. | Mortality ratio (%) 500 ppm |
|---|---|
| 1 | 100 |
| 3 | 100 |
| 5 | 100 |
| 7 | 90 |
| 47 | 100 |
| 48 | 100 |
| 49 | 100 |
| 50 | 100 |
| 51 | 100 |
| 52 | 100 |
| 53 | 100 |
| 55 | 100 |
| 56 | 100 |
| 57 | 100 |
| Comparative agent** | 20 |
| Control agent 1* | 100 |

*2-sec-butylphenyl-N-methylcarbamate (Bassa$^R$)
**1-dimethylcarbamoyl-3-tert-butyl-5-carboethoxyme-thylthio-1H-1,2,4-triazole (Japanese Unexamined Patent Publication (Kokai) No. 62-70365)

TEST EXAMPLE 2

Insecticidal effect against *Laodelphox striatellus*

A wettable agent of the present compound formed into a preparation was adjusted to 250 ppm and 50 ppm of the active ingredient by dilution with water. A predetermined amount of the chemical solution was flooded onto the soil of a pot where rice seedlings in the 3-4 leaf stage were planted. After one day, the pot surface was covered, so as not to be in contact with the chemical, and 10 larvae of *Laodelphox striatellus* which were 14 days old were freed therein. After 2 days, the numbers of dead and alive insects were examined, and the mortality ratio was calculated to obtain the results shown in Table 3 (a) and Table 3 (b).

TABLE 3 (a)

| Compound No. | Mortality ratio (%) | |
|---|---|---|
| | 250 ppm | 500 ppm |
| 1 | 100 | 100 |
| 2 | 100 | — |
| 3 | 100 | 80 |
| 5 | 90 | 70 |
| 6 | 60 | — |
| 7 | 100 | — |
| 9 | 60 | — |
| Comparative agent | 0 | 0 |
| Control agent 1 | 100 | 100 |

TABLE 3 (b)

| Compound No. | Mortality ratio (%) 500 ppm |
|---|---|
| 47 | 100 |
| 48 | 100 |
| 49 | 100 |
| 50 | 100 |
| 51 | 100 |
| 52 | 100 |
| 53 | 100 |
| 55 | 100 |
| 56 | 100 |

TEST EXAMPLE 3

Insecticidal effect against aphid

A wettable agent of the present compound formed into a preparation was adjusted to 500 ppm and 125 ppm of the active ingredient by dilution with water. Onto the soil in a pot where cucumber young seedlings were planted and inoculated with cotton aphid, the chemical solution was flooded in a predetermined amount. After 4 days, the number of aphids living on the leaf surface was examined, and the mortality ration was calculated from the number of insects provided for the test before the treatment. The results are shown in Table 4 (a) and Table 4 (b).

TABLE 4 (a)

| Compound No. | Mortality ratio (%) | |
|---|---|---|
| | 500 ppm | 125 ppm |
| 1 | 100 | 100 |
| 3 | 100 | 98 |
| 5 | 100 | 100 |
| 7 | 100 | 100 |
| 47 | 100 | 100 |
| 48 | 100 | 100 |
| 49 | 100 | 80 |
| 50 | 100 | 100 |
| 51 | 100 | 100 |
| 52 | 100 | 80 |
| 53 | 100 | 100 |
| 54 | 100 | 50 |
| 55 | 100 | 100 |
| 56 | 95 | 60 |
| 57 | 100 | 100 |
| Comparative agent | 48 | 18 |
| Control agent 2* | 100 | 100 |

Control agent 2* = O,S-dimethyl-N-acetylphosphoro-amidothioate (Ortran$^R$)

TABLE 4 (b)

| Compound No. | Mortality ratio (%) 500 ppm |
|---|---|
| 18 | 100 |
| 19 | 100 |
| 20 | 100 |
| 21 | 100 |
| 22 | 100 |
| 23 | 100 |
| 24 | 100 |
| 25 | 100 |
| 26 | 100 |
| 27 | 100 |
| 28 | 100 |
| 30 | 100 |
| 31 | 100 |
| 32 | 100 |
| 33 | 100 |
| 34 | 100 |
| 35 | 100 |
| 37 | 100 |
| 38 | 100 |
| 39 | 100 |
| 40 | 100 |
| 41 | 100 |
| 42 | 100 |
| 43 | 100 |
| 44 | 100 |
| 45 | 100 |

TEST EXAMPLE 4

Insecticidal effect against *Musca domestica*

The present compound was controlled to 100 ppm of the active ingredient by dilution with acetone.

One ml of the chemical solution was added dropwise to a glass laboratory dish with a diameter of 9 cm and dried in air. After air drying, 15 female adult insects of *Musca domestica* were freed into the laboratory dish, and left to stand in a thermostatic chamber at 25° C. After 24 hours, the numbers of dead and alive insects were examined, and the mortality ratio was calculated to obtain the results shown in Table 5.

TABLE 5

| Compound No. | Mortality ratio (%) 100 ppm |
|---|---|
| 1 | 100 |
| 2 | 100 |
| 3 | 97 |
| 47 | 100 |
| 48 | 100 |
| 49 | 100 |
| 50 | 100 |
| 51 | 100 |
| 52 | 100 |
| 53 | 100 |
| 54 | 50 |
| 55 | 100 |
| 56 | 100 |
| 57 | 80 |
| Comparative agent | 97 |
| Control agent 3* | 100 |

Control agent 3* = O,S-dimethyl-o-(3-methyl-4-nitrophenyl)-thiophosphate (Sumithion$^R$)

TEST EXAMPLE 5

Insecticidal effect against plant parasitic nematode

Granules of the present product were formed into a preparation which was uniformly mixed with a soil contaminated with sweet potato root-knot nematode in a Wagner pot of 1/5000 to 3 kg of the active ingredient per 10 a.

One day after mixing, 5 grains each of cucumber seeds were seeded, and the formation ratio of root-knots formed at the cucumber root portion (root-knot index) was examined. The root-knot control ratio was calculated according to the following formula, to obtain the results shown in Table 6 (a) and Table 6 (b).

$$\text{Control }(\%) = \frac{\text{Sum of root-knot indices in each root}}{4 \times \text{number of roots examined}} \times 100$$

TABLE 6 (a)

| Compound No. | Root-knot control ratio (%) |
| --- | --- |
| 1 | 75.8 |
| 2 | 68.0 |
| 3 | 73.3 |
| 4 | 66.6 |
| 5 | 93.3 |
| 6 | 73.3 |
| 7 | 73.3 |
| 8 | 52.0 |
| 9 | 37.8 |

TABLE 6 (b)

| Compound No. | Root-knot control ratio (%) |
| --- | --- |
| 47 | 100 |
| 48 | 100 |
| 49 | 40 |
| 51 | 75 |
| 53 | 75 |
| 55 | 100 |
| 56 | 40 |

As apparent from the test results described above, the compound of the present invention has a chemical structure different from the triazole type insecticide of the prior art, and has a superior insecticidal spectrum and insecticidal performance.

More specifically, it exhibits a particularly superior insecticidal effect against harmful insects of Diptera, Hemiptera, Tylenchoida, and Aphelenechoida.

We claim:

1. A triazole compound having the formula (I):

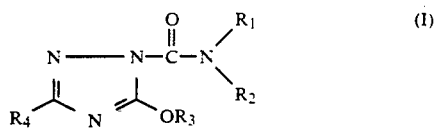

wherein $R_1$ and $R_2$ represent a hydrogen atom, a $C_1$–$C_6$ alkyl group or a dialkylcarbamoyl group having a $C_1$–$C_6$ alkyl group, $R_3$ represents CONRR' where R and R' form a $C_3$–$C_6$ alkylene group which may be substituted with a $C_1$–$C_3$ alkyl group; $R_4$ represents

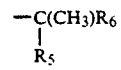

wherein $R_5$ represents a hydrogen atom, a $C_1$–$C_4$ alkyl group, $R_6$ represents a $C_1$–$C_6$ alkyl group or $R_5$ and $R_6$ may be bonded to form a $C_2$–$C_7$ alkylene group; with a proviso that $R_1$ and $R_2$ cannot by dialkylcarbamoyl groups at the same time.

2. A triazole compound as claimed in claim 1, wherein $R_4$ is a t-butyl group.

3. A triazole compound as claimed in claim 1, wherein $R_4$ is a 1-methyl-cyclopropyl group.

4. A triazole compound as claimed in claim 2, wherein each of $R_1$ and $R_2$ is a methyl group.

5. A triazole compound as claimed in claim 3, wherein each of $R_1$ and $R_2$ is a methyl group.

6. An insecticide composition containing a insecticidal effective amount of a triazole compound having the formula (I) of claim 1, as the active ingredient and an inert carrier therefor.

7. An insecticide composition as claimed in claim 6, wherein $R_4$ is a t-butyl group.

8. An insecticide composition as claimed in claim 6, wherein $R_4$ is a 1-methyl-cyclopropyl group.

9. An insecticide composition as claimed in claim 7, wherein each of $R_1$ and $R_2$ is a methyl group.

10. An insecticide composition as claimed in claim 8, wherein each of $R_1$ and $R_2$ is a methyl group.

* * * * *